United States Patent [19]

Shibahara et al.

[11] Patent Number: 4,810,702
[45] Date of Patent: Mar. 7, 1989

[54] ANTIBACTERIAL AGENT FOR MAMMAL USE COMPRISING CEPHALOSPORIN DERIVATIVES AS AN EFFECTIVE INGREDIENT

[75] Inventors: Seiji Shibahara; Tsuneo Okonogi; Yasushi Murai; Toshiaki Kudo; Takashi Yoshida; Ken Nishihata; Shinichi Kondo, all of Yokohama, Japan

[73] Assignee: Meiji Seika Kaisha, Ltd., Tokyo, Japan

[21] Appl. No.: 131,779

[22] Filed: Dec. 11, 1987

[30] Foreign Application Priority Data

Dec. 18, 1986 [JP] Japan .................. 61-302932

[51] Int. Cl.$^4$ .................. C07D 501/36; A61K 31/545
[52] U.S. Cl. .................. 514/206; 540/225; 540/226; 540/227
[58] Field of Search .................. 540/227, 225, 226; 514/206

[56] References Cited

U.S. PATENT DOCUMENTS 4,621,081 11/1986 O'Callaghan et al. .............. 540/227

Primary Examiner—Nicholas S. Rizzo
Attorney, Agent, or Firm—Frank J. Jordan; C. B. Hamburg; Manabu Kanesaka

[57] ABSTRACT

Cephalosporin compounds having 2-(2-aminothiazol-4-yl)-2{(1S)-carboxyethoxyimino}acetyl group on the side chain at the 7-position thereof and 1-ethylpyridinium-4-ylthiomethyl group on the side chain at the 3-position thereof or non-toxic salts thereof are excellent antibacterial agents for mammals including human. The cephalosporin derivatives have low toxicity.

9 Claims, 3 Drawing Sheets

ANTIBACTERIAL AGENT FOR MAMMAL USE COMPRISING CEPHALOSPORIN DERIVATIVES AS AN EFFECTIVE INGREDIENT

BACKGROUND OF THE INVENTION

1. Field of the Invention

The present invention relates to antibacterial agents for mammals comprising as effective ingredients cephalosporin compounds having 2-(2-aminothiazol-4-yl)-2{(1S)-carboxyethoxyimino}acetyl group on the side chain at the 7-position thereof and 1-ethylpyridinium-4-ylthiomethyl group on the side chain at the 3-position thereof or non-toxic salts thereof.

2. Prior Art

β-Lactam antibacterial agents represented by penicillin and cephalosporin have been widely used for mammals including human. A current serious problem from a clinical viewpoint is appearance of bacteria which are resistant to β-lactam antibacterial agents caused by frequent use of β-lactam anti-bacterial agents.

In recent years, cephalosporins effective for these resistant bacteria have been investigated and compounds having a α-dimethylcarboxymethoxyiminoaminothiazoleacetic acid on the side chain at the 7-position thereof and showing potent activity against Pseudomonas aeruginosa are disclosed in West German Pat. No. 2,921,316. On the other hand, cephalosporins having a more wider and potent antibacterial activity against resistant Gram-positive and Gram-negative bacteria are disclosed in Published Unexamined Japanese Patent Application No. 192394/82. A common characteristic of these compounds is that pyridine or a substituted pyridine is bound to the 3'-position of cephalosporin in the form of quaternary salt on the side chain at the 3-position thereof.

A problem in investigations on an enhanced antibacterial agent of cephalosporin including these prior art lies in that when the antibacterial activity is enhanced against Gram-positive bacteria, the antibacterial activity against Pseudomonas aeruginosa is reduced, whereas when the antibacterial activity against Psuedomons aeruginosa is enhanced, the antibacterial activity against Gram-positive bacteria is reduced.

In order to solve the problem, the present inventors prepared cephalosporin compounds having the asymmetric center on the alkoxy moiety of α-alkoxyiminoaminothiazoleacetic acid present on the side chain at the 7-position and having 1-alkyl-pyridinium-4-ylthiomethyl group at the 3-position which are effective against bacteria including a wide range of resistant bacteria and filed a patent application directed thereto as Japanese Patent Application No. 267984/85 (Japanese Laid-open Patent Publication No. 126189/87). Subsequently, the present inventors have made investigations on the stereochemistry of the alkoxyimino moiety and on the alkyl moiety of 1-alkyl-pyridinium-4-ylthiomethyl group against resistant bacteria, made tests for antibacterial activity in more detail and made animal tests in a wider range, and provided with more practicable compounds as antibacterial agents for mammals including human to solve the problem.

SUMMARY OF THE INVENTION

The present invention is directed to antibacterial compositions for mammals including human comprising as effective ingredients cephalosporin derivatives represented by formula (I):

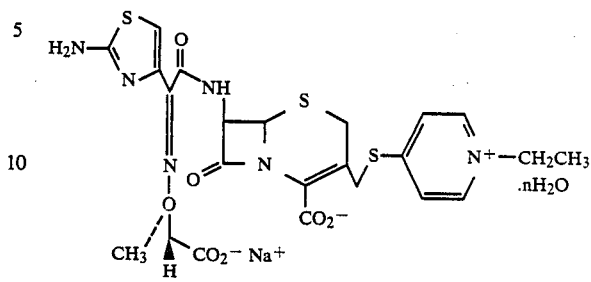

wherein n is 1.0 to 4.0, or non-toxic salts thereof.

DETAILED DESCRIPTION OF THE INVENTION

The non-toxic salts as used herein refer to alkali metal salts such as a sodium salt or potassium salt; basic amino acid salts; or acid addition salts such as hydrochloride, sulfate, methanesulfonate, acetate, acidic amino acid salts, etc.

Various properties of the compounds represented by formula (I) or non-toxic salts thereof in accordance with the present invention are much more excellent as antibacterial agents than that of analogous compounds, explained below in comparison with known compounds.

. Compound I of the present invention as the effective ingredient:

(6R, 7R)-7-[(Z)-2-(2-aminothiazol-4-yl)-2-{(1S)-carboxyethoxyimino} acetamido]-3-(1-ethylpyridinium-4-ylthiomethyl)-ceph-3-em-4-carboxylate monosodium salt Comparative Compound: CAZ (6R, 7R)-7-[(Z)-2-(2-aminothiazol-4-yl)-2-(2-methylcarboxyisoprop;oxyimino)acetamido]-3-pyridinium-1-ylmethyl-ceph-3-em-4-carboxylate (this compound is commercially available under a general name, ceftazidime and disclosed in West German Pat. No. 2,921,316)

Comparative Compound: HR-810
(6R, 7R)-7-[(Z)-2-(2-aminothiazol-4-yl)-2-(methoxyimino) acetamido]-3-cyclopentenopyridinium-1-ylmethyl-ceph-3-em-4-carboxylate
(this compound is disclosed in Published Unexamined Japanese Patent Application No. 192394/82)

Test Example 1

(antibacterial activity in vivo)

The minimum growth inhibitory concentration (MIC) against various bacteria was measured in a bacterial count of $10^6$ CFU/ml using medium SDA (NISSUI) in accordance with the Japan Chemotherapy Association.

The results are shown in Table 1.

TABLE 1

Minimum Growth Inhibitory Concentration

| Bacteria Tested | MIC (mcg/ml) | | |
|---|---|---|---|
| | Compound of This Invention | CAZ | HR-810 |
| Staphylococcus aureus Smith (I) | 1.56 | 3.13 | 0.39 |
| Staphylococcus epidermidis ATCC 14990 | 3.13 | 3.13 | 0.39 |
| Bacillus subtilis ATCC6633 | 3.13 | 3.13 | 0.10 |
| Escherichia coli W3630 RGN823 | 0.05 | 0.20 | 0.10 |
| Escherichia coli W3630 RGN238 | 0.20 | 0.20 | 0.78 |
| Escherichia coli 255 | 0.20 | 12.5 | 0.20 |
| Escherichia coli 255/S-1 | 0.10 | 0.39 | 0.05 |
| Escherichia coli GN206 | 0.10 | 1.56 | <0.025 |
| Citrobacter freundii GN346 | 6.25 | 25 | 0.78 |
| Citrobacter freundii GN346/16-10 | 6.25 | 25 | 0.78 |
| Citrobacter freundii GN346/16 | 0.39 | 0.78 | 0.05 |
| Pseudomonas aeruginosa M-0148 | 0.78 | 1.56 | 12.5 |
| Pseudomonas aeruginosa IAM-1007 | 0.78 | 0.78 | 12.5 |
| Pseudomonas aeruginosa M1 Rms139 | 0.78 | 0.78 | 3.13 |

TEST EXAMPLES 2 TO 4

Method

Each MIC of various bacteria clinically isolated from patients was measured in a manner similar to Test Example 1 and its percentage to the all strains to reach the inhibitory concentration was accumulatively expressed.

TEST EXAMPLE 2

Figure 1:
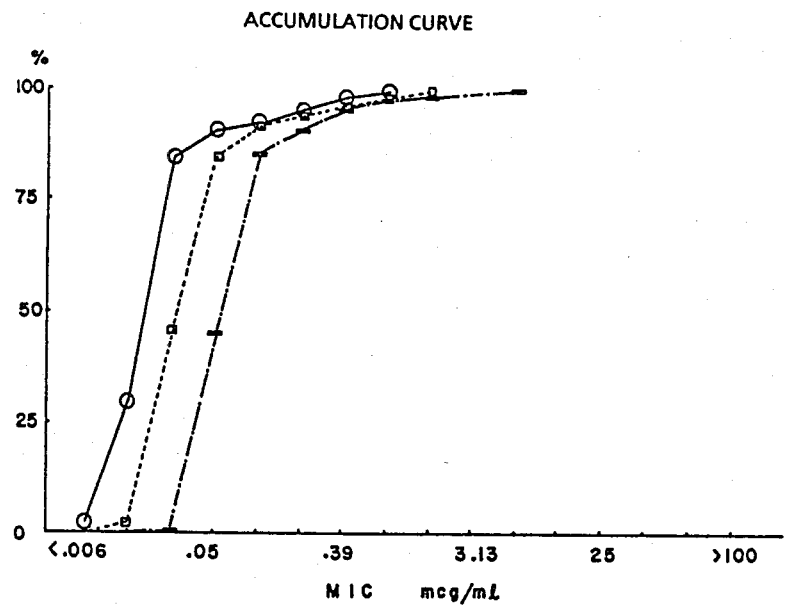
FIG. 1 is a drawing showing results on distribution in sensitivity to clinically isolated pneumobacilli obtained in Test Example 2 using 128 strains of Klebsiella pneumoniae wherein O, □ and ⌑ indicate the compound of the present invention, HR-810 and CAZ, respectively.

Distribution in sensitivity to pneumobacilli clinically isolated.
The results are shown in FIG. 1.

TEST EXAMPLE 3

Figure 2:
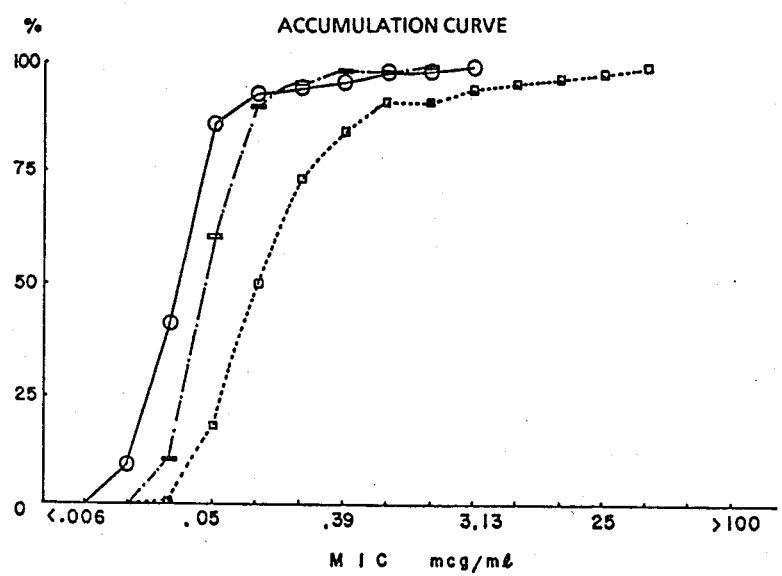
FIG. 2 is a drawing showing results on distribution in sensitivity to a clinically isolated variant obtained in Test Example 3 using 75 strains of Proteus vulgaris wherein O, □ and ⌑ indicate the compound of the present invention, HR-810 and CAZ, respectively.

Distribution in sensitivity to variant clinically isolated. The results are shown in FIG. 2.

TEST EXAMPLE 4

Figure 3:
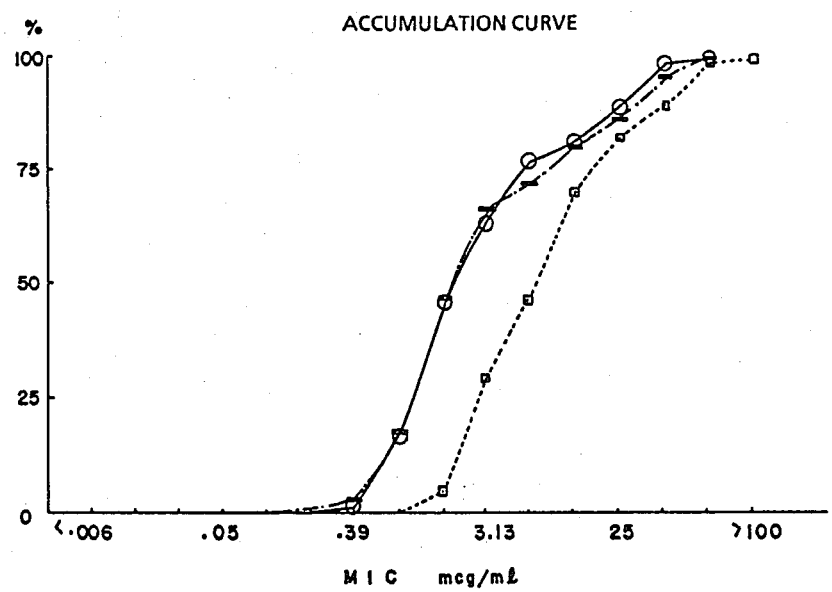
FIG. 3 is a drawing showing results on distribution in sensitivity to clinically isolated Pseudomonas aeruginosa using 100 strains of Pseudomonas aeruginosa wherein O, □ and ⌑ indicate the compound of the present invention, HR-810 and CAZ, respectively.

Distribution in sensitivity to Pseudomonas aeruginosa clinically isolated.
The results ae shown in FIG. 3.

TEST EXAMPLE 5

Acute Toxicity Test 75 mg of each test compound was dissolved in 0.4 ml of phuysiological saline. The solution was administered to the tail vein of ICR strain male mice (mean body weight of 25 g, 5 weeks old) of one group being 3 mice. Observation was made for 14 days.

As a result, all groups administered with Compound I, CAZ, HR-810 survived and it was confirmed that any of these compounds showed $LD_{50}$ of 4 g/kg or more.

TEST.EXAMPLE 6

Effect to prevent infections

The culture solution of each test bacterium was adjusted to a bacterial concentration shown in the table and then supplemented with 2.5% (W/V) of mucin. The solution was intraperitoneally administered to ICR strain male mice (mean body weight of 20 g, 4 weeks old) of one group being 8 at a dose of 0.5 ml to experimentally cause infection. Each test compound was subcutaneously administered one hour after (provided that in case of Pseudomonas aeruginosa was given one hour and 3 hours after). Observation was made for 7 days. The preventive effect $ED_{50}$ value was determined by the Miller and Taiter method and the results are shown in Table 2.

TABLE 2

| Bacteria Tested | Inoculum Size (CFU/mouse) | Compound | MIC (mcg/ml) | $ED_{50}$ (mg/mouse) |
|---|---|---|---|---|
| Escherichia coli GN206 | $9.5 \times 10^6$ | Compound of this invention | 0.20 | 0.36 |
| | | CAZ | 1.56 | 1.0 |
| Pseudomonas aeruginosa GN10362 | $8.8 \times 10^5$ | Compound of this invention | 1.56 | 4.5 |
| | | CAZ | 1.56 | 8 |
| Klebsiella pneumoniae PCI 602 | $6.5 \times 10^4$ | Compound of this invention | 0.05 | 0.33 |
| | | CAZ | 0.20 | 0.57 |
| | | HR-810 | 0.05 | 1.3 |
| Escherichia coli No. 29 | $2.3 \times 10^5$ | Compound of this invention | 0.10 | 0.002 |
| | | CAZ | 0.20 | 0.006 |
| | | HR-810 | 0.05 | 0.006 |

TEST EXAMPLE 7

Concentration in blood plasma (rat)

A test compound was dissolved in physiological saline in a concentration of 20 mg/ml. The solution was given in the tail vein of SD strain male rats (mean body weight of 325 g) of one group being 4 in a dose of 1 ml/kg. Blood was collected from the femoral artery in course of time and blood plasma was isolated from the blood. A concentration of the test compound in blood plasma was quantitatively assayed by high performance liquid chromatography.

Figure 4:
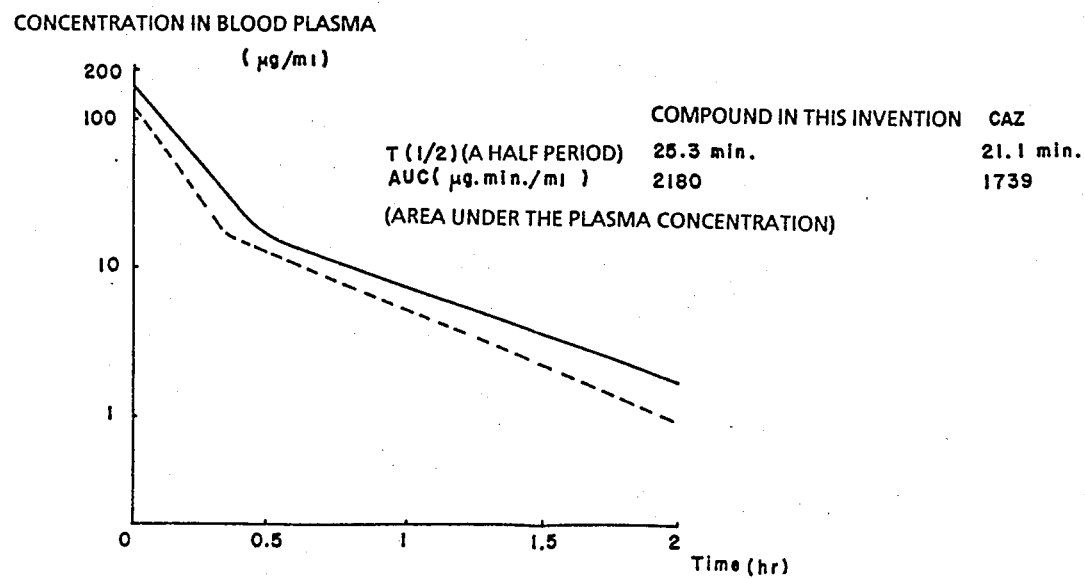
FIG. 4 is a drawing showing results obtained by measuring blood plasma concentration in course of time in Test Example 7, wherein— and . . . indicate the compound of the present invention and CAZ, respectively.

The change of concentration in course of time is shown in FIG. 4.

TEST EXAMPLE 8

Concentration in Serum (common marmoset)

A test compound was dissolved in 0.05M phosphate buffer (pH 6.5) in a concentration of 2.0 mg/ml. The solution was intramuscularly administered to female common marmosets of one group being 2 in a dose of 5 ml/kg.

Figure 5:
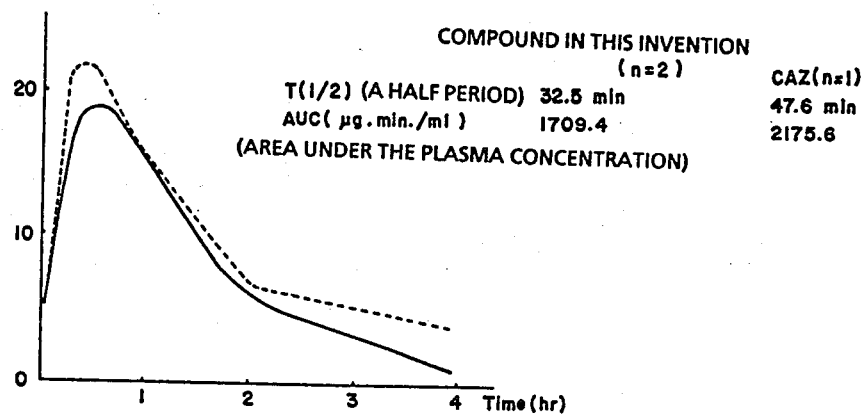
FIG. 5 is a drawing showing results obtained by measuring serum concentration with passage of time in Test Example 8, wherein— and . . . indicate the compound of the present invention and CAZ, respectively.

Blood was collected from the femoral artery with passage of time and serum was separated from the blood followed by quantitative assay by bioassay using Escherichia coli K-12 HW 8236 as a bacterium for the assay. The change in concentration in course of time is shown in FIG. 5.

As is evident from the foregoing test examples, the antibacterial agent comprising the compound represented by formula (I) as a main ingredient in accordance with the present invention exhibits the antibacterial activity over a wide range from Gram-positive bacteria represented by Staphylococcus aureus to Gram-negative bacteria represented by Escherichia coli and Pseudomonas aeruginosa. Particularly as is evident from distribution in sensitivity to clinically isolated strains, the compound of the present invention exhibits a much more excellent antibacterial activity over a wide range, even when compared to known compounds having different substituents on the side chain at the 7-position and at the 3-position thereof.

Further, the compound of the present invention has a low toxicity and is rapidly transferred into blood and organ and has sufficient durability in a concentration to exhibit the antibacterial activity, as is clearly seen from various animal tests.

Such excellent in vivo antibacterial activity and transferability into the living body are reflected by the effect to prevent infections against experimental infectous disease in Test Example 6. As compared to the known compounds, the compound of the present invention has an effect on Escherichia coli, pneumobacilli and Pseudomons aeruginosa, equal to or superior to them.

As is evident from the foregoing description, the antibacterial agents comprising the compound of the present invention as an effective ingredient are useful for treatment of infections for mammals including human.

Dosage of the antibacterial agent of the present invention varies depending upon age, body weight, condition, route for administration, time to be administered, or the like but the antibacterial agent is generally administered intravenously or intramuscularly in a dose of 0.5 to 3 g/day, preferably 1 to 2 g/day, as the effective ingredient, once or dividing into several times.

The addition of salts of the cephalosporin derivatives represented by general formula (I) are novel compounds and can be prrepared by the following reference examples.

REFERENCE EXAMPLE 1

Preparation Of Raw Compound (For Cephalosporin Having The Side Chain At The 7-Position Thereof)

In 11 ml of dimethylformamide was dissolved 2.16 g of benzhydryl L-lactate. After cooling the solution to −40° C., 0.8 ml of sulfuryl chloride was added thereto followed by stirring for an hour. Thereafter the reaction solution was extracted with ethyl acetate and a sodium bicarbonate aqueous solution. The organic phase was washed with water, dried and then concentrated to dryness to give 1.8 g of benzhydryl (2R)-2-chloropropionate. This ester was reacted with 3.1 g of allyl (Z)-2-hydroxyimino-2-(2-tritylaminothiazol-4-yl)acetate prepared in a manner similar to the description of Published Unexamined Japanese Patent Application No. 149289/80 in 16 ml of dimethylsulfoxide overnight at room temperature in the presence of 1.8 g of potassium carbonate. The reaction solution was partitioned with ice water and ethyl acetate. The organic phase was washed with water, dried and concentrated. The residue was dissolved in 30 ml of methylene chloride. To the solution were added 182 mg of triphenylphosphine and 34 mg of tetrakistriphenylphosphine palladium. The mixture was stirred at room temperature for 30 minutes. Then, a solution of 1.26 g of potassium 2-ethylhexanoate in ethyl acetate. After stirring at room temperature for 2 hours, 45 ml of isopropyl ether was added and the mixture was allowed to stand overnight at 0° C. The obtained precipitates were partitioned in ethyl acetate-acidic water (pH 2.8). The organic phase was washed with water, dried and concentrated to give 2.13 g of 2-(2-tritylamino-thiazol-4-yl)-2-{(1S)-1-diphenylmethoxycarbonylethoxyimino}acetic acid.

$[\alpha]_D^{23}$—10.2 (c=5.0, CHCl$_3$)

REFERENCE EXAMPLE 2

Preparation Of Compound (I) Trifluoroacetate 2.1 g of the aminothiazoleacetic acid derivative prepared in Reference Example 1 and 2 g of p-methoxybenzyl 7-amino-3-chloromethyl-ceph-3-em-4-carboxylate were suspended in methylene chloride. After cooling to 0° C., 0.35 ml of phosphorus oxychloride and 1.45 ml of pyridine were added to the suspension followed by stirring for an hour. Then, the reaction mixture was partitioned in ethyl acetate-saturated saline aqueous solution. THe organic phase was washed with water, dried and concentrated. The residue was dissolved in 12 ml of dimethyl sulfoxide and 510 mg of 1-ethyl-4-thiopyridone was added to the solution. The mixture was stirred at room temperature for an hour. Then, the reaction mixture was partitioned in chloroform-saturated saline aqueous solution. The organic phase was washed with water, dried and concentrated. The formed residue was dissolved in 4.5 ml of anisole. The solution was cooled to 0° C. and 13 ml of trifluoroacetic acid was added thereto. After reacting for an hour, 50 ml of isopropyl ether was added to precipitate. The precipitates were taken by filtration, washed with isopropyl ether and dried to give 2.7 g of (6R, 7R)-7-[(Z)-2-(2-aminothiazol-4-yl)-2-{(1S)-carboxyethoxyimino}acetamido]-3-(1-ethylpyridinium-4-ylthiomethyl)-ceph-3-em-4-carboxylate trifluoroacetic acid salt.

REFERENCE EXAMPLE 3

Preparation Of Compound (I) Monosodium Salt 1 g of Compound (I) trifluoroacetate obtained in Reference Example 2 was dissolved in 5 ml of distilled water. Then, 380 mg of sodium bicarbonate was added to the solution. The mixture was stirred and the pH was adjusted to 7.8. The obtained solution was filtered and the filtrate was packed in a column with 40 ml of porous synthetic adsorbent (HP-20). After washing the column with 80 ml of distilled water, elution was performed with 80 ml of distilled water-methanol (2:1). A fraction containing the product was concentrated to a 10% concentration under reduced pressure and then filtered through a millipore filter. The obtained sterilized filtrate was lyophilized to give 450 mg of (6R, 7R)-7-[(Z)-2-(2-aminothiazol)-4-yl)-2-{(1S)-carboxyethoxyimino}acetamido]-3-(1-ethylpyridinium-4-ylthiomethyl)-ceph-3-em-4-carboxylate sodium salt.

The present invention will be described in more detail with reference to the example below but is not deemed to be limited thereto.

EXAMPLE 1

Preparation Of Compound (I) Dry Powders For Injection

10% Aqueous solution of Compound (I) is aseptically filtered and 1.0 g each of the solution was charged in a vial bottle. The bottle is lyop;hilized as it was. Then, the upper part of the bottle plugged with a rubber stopper and aluminum is wound and fastened around the upper part. Upon use, distilled water for injection was injected with a needle through the rubber stopper to dissolve the content, for use as an injection.

The present invention provides the antibacterial agents comprising as an effective ingredient the cephalosporin compound having the asymmetric center at the alkoxy moiety of 1-alkoxyiminoaminoethiaoleacetic acid on the side chain at the 7-position and the 1-alkyl-pyridinium-4-ylthiomethyl group at the 3-position which have a potent antibacterial activity against bacteria including a wide range of resistant bacteria and can be extremely effective when used for mammals including human.

While the invention has been described in detail and with reference to specific embodiments thereof, it will be apparent to one skilled in the art that various changes and modifications can be made therein without departing from the spirit and scope thereof.

What is claimed is:

1. An antibacterial compound selected from the group consisting of cephalosporin derivatives of the formula:

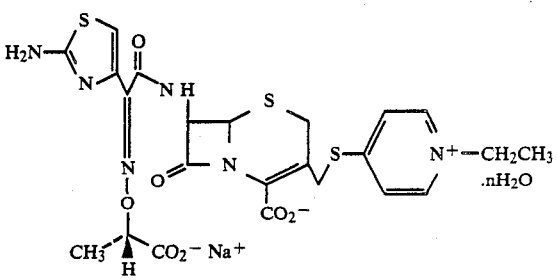

wherein n is 1.0 to 4.0 and a non-toxic salt thereof.

2. An antibacterial compound as claimed in claim 1 which is (6R, 7R)-7-[(Z)-2-(2-aminothiazol-4-yl)-2-}(1S)-carboxyethoxyimino}acetamido]-3-(1-ethyl-pyridinium-4-ylthiomethyl)-ceph-3-em-4-carboxylate.

3. An antibacterial compound as claimed in claim 1 which is (6R, 7R)-7-[(Z)-2-(2-aminothiazol-4-yl)-2-{(1S)-carboxyethoxyimino}acetamido]-3-(1-ethyl-pyridinium-4-ylthiomethyl)-ceph-3-em-4-carboxylate monosodium salt.

4. An antibacterial compound as claimed in claim 1 wherein said non-toxic salt is selected from the group consisting of an alkali metal salt, a basic amino acid salt and an acid addition salt.

5. An antibacterial compound as claimed in claim 4 wherein said alkali metal salt is selected from the group consisting of a sodium salt and a potassium salt.

6. An antibacterial compound as claimed in claim 4 wherein said acid addition salt is selected from the group consisting of a hydrochloride, a sulfate, a methanesulfonate, an acetate and an acidic amino acid salt.

7. A method of treating a bacterial infection in a human or an animal comprising administering 0.5 to 3 g/day of a compound as claimed in claim 1.

8. A method as in claim 7, wherein said compound is administered intravenously.

9. A method as in claim 7, wherein said compound is administered intramuscularly.

* * * * *

UNITED STATES PATENT AND TRADEMARK OFFICE
CERTIFICATE OF CORRECTION

PATENT NO.   : 4,810,702
DATED        : March 7, 1989
INVENTOR(S)  : Seiji Shibahara et al It is certified that error appears in the above-identified patent and that said Letters Patent is hereby corrected as shown below:

On the Title Page, Item [73, in the section of Assignee, add --Susumu Mitsuhashi, Tokyo, Japan Signed and Sealed this Nineteenth Day of September, 1989

Attest:

DONALD J. QUIGG

Attesting Officer

Commissioner of Patents and Trademarks